United States Patent [19]

Fujiso et al.

[11] 4,400,574

[45] Aug. 23, 1983

[54] ISOMERIZATION CATALYST AND PROCESS FOR PRODUCTION THEREOF

[75] Inventors: Tokuo Fujiso, Yokosuka; Soichi Nomura, Tokyo; Tadashi Ohmori, Yokohama, all of Japan

[73] Assignee: Nippon Oil Company, Ltd., Japan

[21] Appl. No.: 309,495

[22] Filed: Oct. 6, 1981

Related U.S. Application Data

[62] Division of Ser. No. 177,510, Aug. 12, 1980, abandoned.

[30] Foreign Application Priority Data

Aug. 15, 1979 [JP] Japan .................................. 54-103199

[51] Int. Cl.³ .............................................. C07C 5/24
[52] U.S. Cl. ...................................... 585/671; 252/442
[58] Field of Search ................ 252/442; 585/671, 664, 585/665, 666, 667, 668, 669, 670

[56] References Cited

U.S. PATENT DOCUMENTS

| | | | |
|---|---|---|---|
| 3,248,448 | 4/1966 | Goble et al. | 585/669 |
| 3,287,439 | 11/1966 | Suggrèt et al. | 585/669 |
| 3,553,281 | 1/1971 | Goble et al. | 252/442 |

FOREIGN PATENT DOCUMENTS

| | | | |
|---|---|---|---|
| 981694 | 1/1965 | United Kingdom | 585/669 |
| 1065005 | 4/1967 | United Kingdom | 585/671 |
| 722886 | 3/1978 | U.S.S.R. | 585/671 |

*Primary Examiner*—Delbert E. Gantz
*Assistant Examiner*—A. Pal
*Attorney, Agent, or Firm*—Wenderoth, Lind & Ponack

[57] ABSTRACT

A process for converting linear aliphatic olefins into branched-chain aliphatic olefins, by contacting said linear aliphatic olefins with a comprising an active alumina carrier and fluorine and chlorine supported thereon, the amounts of fluorine and chlorine supported being 0.2 to 2.0% by weight, and 0.2 to 4.0% by weight, respectively, based on the total weight of the catalyst composition. The aforesaid isomerization catalyst can be produced by contacting an active alumina carrier with at least one halogenated hydrocarbon containing fluorine and chlorine in the molecule at a temperature of 200° to 500° C.

8 Claims, No Drawings

ISOMERIZATION CATALYST AND PROCESS FOR PRODUCTION THEREOF

This is a divisional of Ser. No. 177,510, filed Aug. 12, 1980 now abandoned.

This invention relates to a process for the isomerization catalyst of linear aliphatic olefins, especially with an isomerization catalyst composed of active alumina and halogen supported thereon.

Great quantities of aliphatic olefins are now produced in industrial plants by thermal cracking of naphtha, fluidized catalytic cracking of light oils, etc. It is very desirable to isomerize aliphatic olefins having small amounts of branched chains into those having large amounts of branched chains, or aliphatic olefins having large amounts of branched chains into those having small amounts of branched chains.

For example, a fraction containing n-butene left after separation of butadiene and isobutene from a $C_4$ fraction produced from a plant can be isomerized at the skeleton into useful isobutene. Isobutene is a useful compound which is used, and is expected to be used, in various applications such as raw materials for the production of butyl rubber, methacrylic acid or polybutene and also of methyl tertiary butyl ether which is useful as an automobile auxiliary fuel.

Previously, various phosphoric acid catalysts (British Pat. No. 496,676), halogenated alumina (U.S. Pat. No. 2,471,647), boron-treated alumina (British Pat. No. 1,065,008), various silica-aluminas (U.S. Pat. No. 2,216,284), and various sulfate catalysts (Compt. Revd, Acad. Sci, U.R.S.S. vol. 4, pages 373–376, 1936) have been suggested as catalysts effective for increasing the amount of branched chains of aliphatic olefins, but they have not produced entirely satisfactory results. No catalyst has been discovered up to date which is suitable for conversion on an industrial scale of linear aliphatic olefins, especially $C_4$ or $C_5$ linear aliphatic olefins, into the corresponding branched-chain aliphatic olefins.

It is an object of this invention therefore to provide a catalytic process suitable for isomerizing aliphatic olefins having a small amount of a branched structure to those having a large amount of a branched structure with satisfactory results, and a process for production of the aforesaid catalyst.

A more specific object of this invention is to provide an isomerization catalyst for isomerizing n-butene into isobutene or n-pentene into isopentene with satisfactory results, and a process for producing the aforesaid catalyst.

In accordance with this invention, the above objects are achieved by an isomerization catalyst composition comprising an active alumina carrier and fluorine and chlorine supported thereon, the amounts of said fluorine and chlorine supported being 0.2 to 2.0%, and 0.2 to 4.0%, respectively, based on the total weight of the catalyst composition.

The catalyst composition of this invention can be prepared by contacting at least one halogenated hydrocarbon containing fluorine and chlorine in the molecule with active alumina at a temperature of 200° to 500° C.

The active alumina used in this invention includes theta-alumina, keppa-alumina, delta-alumina, eta-alumina, gamma-alumina, khi-alumina and rho-alumina. Those which are usually employed as catalysts or catalyst carriers are suitable. Desirably, gamma-alumina and eta-alumina are used in this invention. Preferred aluminas have a surface area of at least 200 m²/g, preferably 250 to 350 m²/g, and an $Na_2O$ content of not more than 0.1% by weight, preferably not more than 0.05% by weight. Active alumina produced by calcining alumina hydrate can also be used.

In the present invention, another inorganic oxide may be used together with active alumina in such an amount that the content of the active alumina is at least 50 mole%, preferably at least 70 mole%. Examples of the other inorganic oxide which can be used in combination with active alumina are silica, titania, zirconia, magnesia, chromia, thoria, molybdena, tungsten oxide and iron oxide. At least one of them may be used. Silica, titania and zirconia are preferred. The active alumina and such a compound may be a merely physical mixture, or a chemical bond may occur between active alumina and such an inorganic oxide, as in silica-alumina, zirconia-alumina, magnesia-alumina (spinel), chromia-alumina, thoria-alumina, and alumina-molybdena.

The catalyst of this invention is the one in which 0.2 to 2.0% by weight, preferably 0.5 to 1.5% by weight, of fluorine and 0.2 to 4.0% by weight, preferably 0.5 to 3.0% by weight, of chlorine, all based on the total weight of the catalyst, are deposited on a carrier composed of active alumina or both the active alumina and the other inorganic oxide.

Deposition of fluorine and chlorine on the carrier can be easily effected by treating the carrier composed of active alumina or both active alumina and the other inorganic oxide with a halogenated hydrocarbon containing fluorine and chlorine. Preferably, prior to this treatment, the carrier is allowed to stand for at least 20 hours, preferably at least 40 hours in a gas containing moisture, for example nitrogen or air, at a temperature ranging from room temperature to 100° C. to cause adsorption of moisture to the carrier, and before the halogenation treatment, the carrier which has adsorbed moisture thereto is dried at 350° to 600° C., preferably 400° to 550° C., for 0.1 to 50 hours, preferably 0.2 to 20 hours, in an atmosphere or stream of a gas such as air or nitrogen.

The catalyst prepared by using active alumina which has been subjected to these operations of water absorption and dehydration has a greatly improved activity of catalyzing an isomerization reaction for imparting a branched structure to an aliphatic olefin or increasing the content of the branched structure.

The halogenated hydrocarbon containing fluorine and chlorine used in this invention is an aliphatic hydrocarbon consisting of carbon, fluorine and chlorine, or an aliphatic hydrocarbon consisting of carbon, hydrogen, fluorine and chlorine. Suitable halogenated hydrocarbons are those of the following formula $$C_m H_n F_x Cl_y \tag{I}$$

wherein m is 1 to 2, n is 0 to 2, x is 1 to 5, and y is 1 to 5, provided that $m+1=(n+x+y)/2$.

Suitable ones for use in the present invention are e.g. $CHClF_2$, $CCl_2F_2$, $CClF_3$, $CHCl_2F$, $CCl_3F$, $CH_2ClF$, $CCl_2F$—$CCl_2F$, $CCl_2F$—$CCl_2$ and $CF_3$—$CClF_2$.

Catalysts obtained by treatment with halogenated hydrocarbons containing either one of fluorine or chlorine do not give satisfactory results in regard to activity, selectivity and activity duration in the aforesaid isomerization reaction.

For example, when a catalyst is used which is obtained by treating active alumina with a fluorinated hydrocarbon containing fluorine alone, such as tetrafluoromethane, trifluoromethane or difluoromethane, as described in British Pat. No. 1,065,005, or a catalyst is used which is obtained by subjecting active alumina to treatment of moisture adsorption and partial dehydration and then treating it with a fluorinated hydrocarbon containing fluorine alone as described in British Pat. No. 1,065,009, side reactions such as polymerization, disproportionation, hydrogen transfer and decomposition occur frequently and the duration of the activity of the catalyst is short as compared with the use of the catalyst of this invention.

In addition, when the alumina carrier is treated with a halogenated hydrocarbon containing both fluorine and chlorine in accordance with this invention, fluorine can be deposited in a larger amount than when it is treated with a halogenated hydrocarbon containing fluorine alone, although no clear reason can be assigned to it. The catalyst halogenated in accordance with this invention is characterized by containing both fluorine and chlorine.

The halogenation treatment of the carrier in this invention is carried out in the gaseous phase using the above-exemplified halogenated hydrocarbon containing fluorine and chlorine. A suitable treating method comprises passing a stream of a halogenated hydrocarbon containing fluorine and chlorine, with or without dilution with an inert gas such as nitrogen or a non-reducing gas such as air, over the active alumina carrier to be treated. The principal halogenating factors of the halogenating conditions are the treating temperature and time which affect the amounts of fluorine and chlorine to be deposited. The amounts of fluorine and chlorine to be supported are also affected by the type, amount, physical properties and shape of the active alumina used, and also by the type and flow rate of the hydrocarbon used, and the type and amount of the diluent.

The suitable halogenating temperature is 200° to 500° C., preferably 350° to 450° C. when the treating temperature is lower than 200° C., the rate of halogenation of the active alumina is slow, and sufficient halogenation does not take place. Thus, the effect of increasing the activity of alumina is not sufficient, and the process is not economical. When the halogenation is carried out for a long period of time at a temperature exceeding 500° C., inactive substances such as crystalline aluminum fluoride occur in the catalyst, and the effect of increasing its activity is not sufficient.

The halogenating time can be accurately determined depending upon the amounts required of fluorine and chlorine. Usually, it is from several minutes to several hours.

When the halogenation is carried out using a halogenated hydrocarbon diluted with an inert gas such nitrogen or a non-reducing gas such as air, the ratio of dilution is not critical, but for practical purposes, the ratio of the diluting gas to the halogenated hydrocarbon is from 0.5 to 20. By using the diluted halogenated hydrocarbon, it is possible to control the halogenation temperature. In order to perform the halogenation treatment under mild reaction conditions and thus to deposit the halogens more uniformly, water may be present in the carrier gas. The amount of the water that may be present in the treating gas is 5 to 1000 mole ppm, preferably 10 to 500 mole ppm. Furthermore, to perform temperature control of the halogenation treatment more easily and deposit the halogens more uniformly on the carrier, the halogenation is preferably performed in a fluidized bed of active alumina. But this can also be performed in a fixed bed of active alumina.

The pressure for the halogenation treatment is not particularly restricted. It is desirable to avoid pressures at which the hydrocarbon containing fluorine and chlorine may condense on the catalyst. Preferably, the halogenation treatment is carried out at atmospheric pressure or pressures near it.

When active alumina is treated with the hydrocarbon containing fluorine and chlorine, the amounts of fluorine and chlorine deposited increase as the halogenation treating conditions become severer, namely as the temperature becomes higher, the time becomes longer and the concentration of the treating agent becomes higher.

When the amounts of fluorine and chlorine deposited are less than 0.2% by weight, the amount of isobutene formed by isomerizing n-butene with the catalyst of this invention, is much the same as that obtained when alumina alone is used as a catalyst. Thus, the effect of halogenation is scarcely noted. On the other hand, when the amount of fluorine exceeds 2.0% by weight and the amount of chlorine exceeds 4.0% by weight in the catalyst of this invention, side-reactions preferentially take place, and the amounts of products having lower or higher boiling points than $C_4$ hydrocarbons increase abruptly.

The catalyst produced by the process of this invention exhibits a marked effect when used for isomerization reaction of obtaining branched-chain aliphatic olefins.

A method has been well known for producing a catalyst for conversion of hydrocarbons by fluorinating active alumina with hydrogen fluoride, fluorine gas, a fluorine-containing compound, etc., or by chlorinating it with hydrogen chloride, chlorine gas, a chlorine-containing gas, etc.

A method is also known which comprises including fluorine and chlorine into active alumina or a substance containing it. For example, Japanese Patent Publication No. 1164/65 discloses a method for isomerizing a double bond of an olefin using a catalyst obtained by supporting an alkali metal or alkaline earth metal on active alumina, and treating the supported active alumina with a halogenated hydrocarbon containing fluorine and chlorine. Japanese Patent Publication No. 11605/64 discloses a method for catalytic disproportionation and rearrangement of a fluorine-containing alkane which comprises using a catalyst obtained by treating alumina with a lower fluorinated hydrocarbon optionally containing chlorine. Japanese Patent Publication No. 27748/68 discloses the same method as in Japanese Patent Publication No. 11605/64 in which, however, a catalyst obtained by treating alumina with a chlorine-containing compound and then with a fluorine-containing compound is used. U.S. Pat. No. 3,287,439 (1966) discloses a method of isomerizing paraffins using a catalyst prepared by treating platinum-supported alumina with a chlorofluorocarbon. Japanese Patent Publication No. 7655/76 discloses the use of a catalyst prepared by treating crystalline aluminosilicate with a hydrocarbon containing fluorine and/or chlorine in the disproportionation reaction of toluene.

These prior art documents do not at all state what activity a catalyst obtained by treating active alumina with a hydrocarbon containing fluorine and chlorine exhibits in an isomerization reaction of an aliphatic olefin to increase the content of a branched structure.

None of them disclose a process for preparation of the special catalyst of this invention.

The linear aliphatic olefin to be isomerized by the catalyst of this invention is an aliphatic olefin usually having 4 to 24 carbon atoms, preferably 4 to 6 carbon atoms. It may be a single compound or a mixture of two or more compounds. Or a mixture of it with a saturated hydrocarbon can be favorably used. Preferably, prior to the isomerization reaction, acetylene or dienes in the starting hydrocarbon are removed completely or almost completely by extraction, selective hydrogenation, etc. This is desirable in view of the duration of the activity of the catalyst.

Most preferably, the catalyst obtained by this invention is used in isomerizing n-butene to isobutene, and is also suitably used to isomerize n-pentene to isopentene.

The isomerization reaction using the catalyst of this invention may be performed by reacting an aliphatic olefin alone or a hydrocarbon mixture containing it with or without dilution with a diluting gas such as nitrogen, carbon dioxide, helium or hydrogen. The reaction is carried out at a temperature of 200° to 600° C., preferably 350° to 550° C. When the reaction temperature is lower than 200° C., the reaction does not sufficiently take place, and when it is higher than 600° C., side reactions such as disproportionation, hydrogen transfer or decomposition take place vigorously.

The reaction pressure is usually atmospheric pressure or a pressure near it. Any pressure may be used which is sufficient to maintain the reactant gases in the gaseous state. The rate of feeding the material, interms of the gas hourly space velocity (GHSV), is 100 to 10,000 V/V/hr, preferably 300 to 3,000 V/V/hr, based on the aliphatic olefin. The selectivity of the isomerization reaction can be increased by causing a small amount of moisture to be present in the reaction system.

In the production of the catalyst by the process of this invention and the isomerization of an olefin using the resulting catalyst, the carrier or the catalyst may be used as a fixed bed or fluirized bed. The reaction is preferably carried out in the gaseous phase.

As described hereinabove, the catalyst of this invention exhibits very high activity in the isomerization reaction of obtaining branched aliphatic olefins from linear aliphatic olefins. The activity of the catalyst lasts very long, and the stability of the activity is high, and the catalyst can be easily regenerated. The catalyst is effective for production of branched-chain aliphatic olefins simply and economically.

The following Examples illustrate the present invention more specifically.

EXAMPLE 1

Commercially available ketjen B type alumina (by an X-ray diffraction analysis, found to be boehmite gel, $Na_2O$ 0.07% by weight, $SO_4$ 0.8% by weight, $SiO_2$ 0.9% by weight, Fe 0.03% by weight; surface area 340 $m^2/g$) was compression-molded into tablets each having a size of 2 mm $\phi \times 2$ mm. The tablets were pulverized to a size of 20 to 30 mesh, and calcined in an electric furnace in a dry nitrogen atmosphere at 500° C. for 4 hours. After cooling, the calcined product was taken out, and allowed to stand indoors for 3 days. After standing, the product showed a weight increase of 10.4% by weight as compared with the weight immediately after firing. Eleven grams of the resulting product was filled in a quartz reaction tube (10 mm $\times$ 500 mm), and dried by passing dry nitrogen at a flow rate of 100 ml/min. at 500° C. for 1.5 hours. After drying, $CCl_2F_2$ gas and nitrogen were passed through the tube at a flow rate of 5.0 ml/min. and 100 ml/min., respectively, for 10 minutes to halogenate the alumina. After the treatment, the catalyst contained 0.74% by weight of fluorine and 1.38% by weight of chlorine. This catalyst is designated X.

Using the catalyst X, 1-butene was isomerized. The starting material was 1-butene (containing 1.5 mole% of n-butane) having a purity of 98.1 mole% diluted to two times with nitrogen. The reaction was carried out at a temperature of 500° C. under atmospheric pressure at a GHSV of 1000.

One hour after the beginning of the reaction, the reaction product contained 2.5% by weight of hydrocarbons having less than 4 carbon atoms ($<C_4$), 61.9% by weight of n-butene, 25.2% by weight of i-butene, 2.9% by weight of n-butane, and 7.5% by weight of hydrocarbons having more than 4 carbon atoms ($>C_4$). Thus, the catalyst X exhibited very high activity.

EXAMPLE 2

Ketjen B alumina molded and pulverized in the same way as in Example 1 was calcined in an air atmosphere at 500° C. for 4 hours, cooled, and allowed to stand in the air for 100 hours. After standing, the alumina was weighed. A weight increase of 10.8% was noted. After standing, the alumina was calcined in an air atmosphere at 500° C. for 4 hours to liberate almost all moisture absorbed during standing. The alumina was calcined, and then allowed to stand in the air for 72 hours to cause absorption of water again. A weight increase of 10.4% was noted as compared with the weight of alumina immediately after the second calcination. After standing, 11 g of the treated alumina was filled into a quartz reaction tube, and dried by passing nitrogen at a flow rate of 250 ml/min. and a temperature of 500° C. for 1.5 hours. Then, $CHClF_2$ and nitrogen containing 200 ppm of moisture were passed through the tube at a flow rate of 2.5 ml/min., and 250 ml/min. respectively, for 25 minutes to halogenate the alumina. The resulting catalyst is designated Y.

After the halogenation treatment, nitrogen was passed at the same temperature and the same flow rate for 1 hour, and equal amounts of n-butenes (1-butene:2-butene=1/1 mole/mole) and nitrogen were contacted with each other at at temperature of 500° C. and atmospheric pressure while maintaining the GHSV of the gaseous mixture at 1500. One hour after the beginning of the reaction, the reaction mixture contained 1.3% by weight of $<C_4$, 54.6% by weight of n-butene, 35.5% by weight of i-butene, 2.2% by weight of butane, and 5.9% by weight of $>C_4$.

COMPARATIVE EXAMPLE 1

Ten grams of alumina (Neobead C, a product of Mizusawa Chemical Co., Ltd.; both $Na_2O$ and $SiO_2$ 0.0 wt.%; surface area 230 $m^2/g$) was put into a quartz reaction tube, and calcined at 450° C. for 1 hour while passing nitrogen at a GHSV of 500 $hr^{-1}$. After the calcination, the alumina was taken out indoors, and allowed to stand for 2 days to cause adsorption of water (weight increase 8.4% by weight). After standing, the alumina was again packed into a quartz reaction tube, and dried by passing nitrogen at a GHSV of 500 $hr^{-1}$ and at a temperature of 450° C. for 1.5 hours. Then, it was fluorinated with $CF_4$ at the same flow rate as nitrogen at 300° C. for 30 minutes using a mixture of nitrogen and $CF_4$. The proportion of fluorine deposited was 0.83% by weight. The resulting catalyst is designated Z.

The same starting material as in Example 1 was passed through the catalyst Z under the same conditions as in Example 1. One hour after the beginning of the reaction, the reaction product contained 0.5% by weight of $<C_4$, 85.3% by weight of n-$C_4'$, 13.8% by weight of i-$C_4'$, 0.2% by weight of n-$C_4$, and 0.2% by weight of $>C_4$. The catalyst Z had lower activity than the catalyst X.

larger amounts of halogen than the specified limit are used, side reactions such as decomposition and/or polymerization preferentially take place to increase the amounts of hydrocarbons having higher or lower boiling points than $C_4$ hydrocarbons.

On the other hand, the catalysts C to G of this invention have excellent selectivity for isobutene, and the amounts of by-products are small.

TABLE 1

|  | Catalyst | The catalyst treating time (minutes) and the amounts of halogens in the catalyst (wt. %) | | | Composition of the reaction product (wt. %) (*) | | | |
|---|---|---|---|---|---|---|---|---|
|  |  | Treating time | Fluorine | Chlorine | $<C_4$ | n-Butene | i-Butene | $>C_4$ |
| Comparative Example 2 | A | 0 | 0 | 0 | 0.2 | 84.1 | 10.6 | 3.6 |
| Comparative Example 3 | B | 2 | 0.15 | 0.30 | 0.2 | 83.6 | 11.6 | 2.8 |
| Example 3 | C | 5 | 0.30 | 0.60 | 0.5 | 75.6 | 19.8 | 2.3 |
| Example 4 | D | 10 | 0.56 | 1.05 | 0.4 | 72.6 | 24.8 | 2.5 |
| Example 5 | E | 14 | 0.78 | 1.50 | 0.4 | 59.2 | 37.0 | 3.3 |
| Example 6 | F | 17 | 0.98 | 1.85 | 0.6 | 58.1 | 38.0 | 4.2 |
| Example 7 | G | 28 | 1.56 | 2.13 | 2.9 | 49.1 | 34.7 | 11.5 |
| Comparative Example 4 | H | 44 | 2.51 | 3.22 | 12.8 | 36.6 | 25.7 | 19.6 |
| Comparative Example 5 | I | 60 | 3.39 | 3.45 | 27.4 | 25.9 | 19.8 | 17.7 |

(*) The remainder of the product consisted mainly of $C_4$ paraffins.

EXAMPLES 3 TO 7 AND COMPARATIVE EXAMPLES 2 TO 5

Commercially available Ketjen B type alumina (by an X-ray diffraction analysis, found to be boehmite gel, powder $Na_2O$ 0.07% by weight, $SO_4$ 0.8% by weight, $SiO_2$ 0.9% by weight, Fe 0.03% by weight; surface area 340 $m^2/g$) was calcined in a dried air atmosphere at 550° C. for 16 hours, and then compression molded into tablets having a size of 2 mm$\phi \times$2 mm. The tablets were pulverized to a size of 20 to 30 mesh. Ten grams of the pulverized alumina was packed into a quartz reaction tube, and dried by passing dry nitrogen at a flow rate of 100 ml/min. at 400° C. for 1.5 hours. The dried alumina was then treated with $CCl_2F_2$ gas and nitrogen at a flow rate of 5 ml/min. and 100 ml/min. at 400° C. for each of the time periods indicated inn Table 1. Thus, eight catalysts having different halogen contents were prepared.

These catalysts were cooled in a nitrogen atmosphere and stored in a sealed condition. The fluorine contents of these catalysts were 0.15 to 3.39% by weight, and the chlorine content of these catalysts were 0.25 to 4.16% by weight.

These eight catalysts and Ketjen B type alumina subjected to the calcination treatment but not to halogenation treatment were tested for activity. The starting material used was 1-butene having a purity of 98.1 mole% (containing 1.5 mole% of n-butene) diluted to two times with nitrogen. The isomerization reaction was performed at a temperature of 500° C. and atmospheric pressure while maintaining the GHSV at 1500 $hr^{-1}$. The results obtained one hour after the beginning of the reaction are shown in Table 1.

It is seen from Table 1 that when a catalyst B obtained by halogenation but containing less than 0.2% by weight of fluorine is used, the amount of isobutene formed is much the same as in the case of using alumina alone, and the effect of halogenation can scarcely been noted. Furthermore, when catalysts H and I having

EXAMPLE 8 AND COMPARATIVE EXAMPLE 6

Thirty grams of commercially available alumina (Neobead C; small spheres 60 to 140 mesh, both $Na_2O$ and $SiO_2$ 0.0% by weight; surface area 230 $m^2/g$) was put into a quartz reaction tube for a fluidized bed, and dried in a stream of air at 500° C. for 4 hours. Then, the temperature was lowered to 400° C., and alumina was fluidized with nitrogen at a flow rate of 3.5 liters/mm, and $CHClF_2$ was entrained at a flow rate of 5 ml/min. for 30 minutes to halogenate the alumina. The resulting treated catalyst contained 1.3% by weight and 0.94% by weight of fluorine and chlorine respectively. The resulting catalyst was designated catalyst J.

For comparison, alumina was treated under the same conditions as above except that the halogenation temperature was changed to 550° C. Thus, a catalyst K was obtained. The catalyst K contained 2.30% by weight of fluorine and 4.36% by weight of chlorine.

The isomerization reaction was carried out using these catalysts J and K under the same conditions using the same starting material as in Examples 1 to 5.

The results are shown in Table 2.

TABLE 2

|  | Catalyst | Amounts of halogen in the catalyst (wt. %) | | Composition of the reaction product (wt. %) | | | |
|---|---|---|---|---|---|---|---|
|  |  | F | Cl | $<C_4$ | Bu-tane | n-Bu-tene | i-Bu-tene | $>C_4$ |
| Example 8 | J | 1.30 | 0.94 | 0.6 | 2.2 | 59.5 | 33.2 | 4.7 |
| Comparative Example 6 | K | 2.30 | 4.36 | 13.6 | 8.2 | 37.1 | 22.3 | 18.8 |

EXAMPLE 9

Commercially available alumina (Neobead D; 91% by weight of $Al_2O_3$ and 9% of $SiO_2$) was pulverized to a size of 20 to 60 mesh, and 13 g of the pulverized alumina was filled into a quartz reaction tube. $N_2$ and $CClF_2\text{-}CCl_2F$ were passed through the reaction tube at a flow rate of 100 ml/min., and 5 ml/min., respectively, at 350° C. for 1 hour to afford a catalyst L. The catalyst L contained 0.89% by weight of fluorine, and 1.21% by weight of chlorine. Using 10 g of the catalyst, n-butene (containing 68.2 mole% of butene-1, 31.3 mole% of butene-2, and 0.5 mole% of n-butane) was reacted at 450° C. under atmospheric pressure while maintaining the GHSV of $C_4/N_2$ (1:2 mole/mole) at 1500. Two hours later, the reaction product contained 0.2% by weight of $<C_4$, 67.6% by weight of n-butene, (18.7% by weight of butene-1 and 48.8% by weight of butene-2), 29.6% by weight of i-butene, and 0.4% by weight of $>C_4$.

COMPARATIVE EXAMPLE 7

Ketjen B type alumina was treated in the same way as in Examples 3 to 7 except that $CF_4$ was used as the halogenated hydrocarbon. The resulting catalyst contained 1.07% by weight of fluorine. This catalyst is designated M. Using the catalyst M, n-butene was reacted under the same conditions as in Examples 1 to 5 using the same starting materials as used in Examples 1 to 5. One hour after the beginning of the reaction, the reaction product contained 0.8% by weight of $<C_4$, 83.8% by weight of n-butene, 13.8% by weight of i-butene, 0.3% by weight of $>C_4$ and 1.8% by weight of butanes. It is clear that the catalyst M had lower activity than the catalysts treated with hyrocarbons containing both fluorine and chlorine as halogens.

EXAMPLE 10

Commercially available Ketjen B type alumina (by an X-ray diffraction analysis, found to be boehmite gel; powder $Na_2O$ 0.07% by weight, $SO_4$ 0.8% by weight, $SiO_2$ 0.9% by weight, Fe 0.03% by weight; surface area 340 $m^2/g$) was calcined in a dry air atmosphere at 550° C. for 16 hours. It was then compression-molded into tablets having a size of 2 mm$\phi \times$2 mm, and pulverized to a size of 20 to 30 mesh. Ten grams of the pulverized alumina was filled into a quartz reaction tube, and dried by passing dry nitrogen at a flow rate of 100 ml/min. and a temperature of 400° C. for 1.5 hours. Then, nitrogen and $CCl_2F_2$ gas were passed at a flow rate of 100 ml/min. and 5 ml/min., respectively, to treat the alumina for 2 to 60 minutes to prepare a catalyst N.

The catalyst N was cooled in a nitrogen atmosphere and stored in a sealed condition. The catalyst contained 0.98% by weight of fluorine and 1.62% by weight of chlorine.

Using the resulting catalyst, 1-pentene was reacted. Ten grams of the catalyst N was filled into a quartz reaction tube, and 1-pentene was passed through the reaction tube at 420° C. and atmospheric pressure while maintaining the LHSV at 6.0. One hour later, the reaction product was recovered, and analyzed for composition. It was found that the reaction product contained 2.3% by weight of $<C_5$, 54.3% by weight of n-pentene, 42.6% by weight of i-pentene and 0.8% by weight of $>C_5$.

What we claim is:

1. A method for converting a linear aliphatic olefin into a branched-chain aliphatic olefin, which comprises contacting at a temperature of 350° to 550° C. said linear aliphatic olefin with a catalyst composition consisting essentially of an active alumina carrier with fluorine and chlorine supported thereon, the amounts of fluorine and chlorine supported being 0.2 to 2.0% by weight, and 0.2 to 4.0% by weight, respectively, based on the total weight of the catalyst composition.

2. The method of claim 1 wherein the linear and branched-chain aliphatic olefin has 4 or 5 carbon atoms.

3. The method of claim 1 wherein said catalyst further comprises at least one oxide selected from the group consisting of silica, titania, zirconia, magnesia, chromia, thoria, molybdena, tungsten oxide and iron oxide.

4. The method of claim 1 wherein said catalyst is produced by a process which comprises contacting an active alumina carrier with at least one halogenated hydrocarbon containing fluorine and chlorine in the molecule at a temperature of 200° to 500° C.

5. The method of claim 4 wherein prior to contacting the carrier with the halogenated hydrocarbon, the carrier is contacted with a water-containing gas to cause adsorption of water on the carrier, and the carrier having adsorbed water thereon is dried at a temperature of 350° to 600° C. for a period of 0.1 to 50 hours.

6. The process of claim 4 wherein the halogenated hydrocarbon containing fluorine and chlorine is a compound expressed by the general formula $$C_mH_nF_xCl_y$$

wherein m is 1 to 2, n is 0 to 2, x is 1 to 5 and y is 1 to 5, provided that $m+1=(n+x+y)/2$.

7. The process of claim 1 wherein said linear aliphatic hydrocarbon is admixed with a diluent gas.

8. The process of claim 1 wherein said diluent gas is nitrogen, carbon dioxide, helium or hydrogen.

* * * * *